US011217184B2

(12) United States Patent
Zeinstra

(10) Patent No.: US 11,217,184 B2
(45) Date of Patent: Jan. 4, 2022

(54) DISPLAY UNIT AND A METHOD OF OPERATING THE SAME

(71) Applicant: KONINKLIJKE PHILIPS N.V., Eindhoven (NL)

(72) Inventor: Michiel Hans Zeinstra, Blauwhuis (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 16/632,557

(22) PCT Filed: Jul. 23, 2018

(86) PCT No.: PCT/EP2018/069935
§ 371 (c)(1),
(2) Date: Jan. 21, 2020

(87) PCT Pub. No.: WO2019/020573
PCT Pub. Date: Jan. 31, 2019

(65) Prior Publication Data
US 2020/0160797 A1    May 21, 2020

(30) Foreign Application Priority Data

Jul. 25, 2017    (EP) .................................... 17182980

(51) Int. Cl.
G09G 3/36    (2006.01)
G09G 3/34    (2006.01)

(52) U.S. Cl.
CPC ............. G09G 3/3406 (2013.01); G09G 3/36 (2013.01); G09G 2320/0653 (2013.01)

(58) Field of Classification Search
CPC .................. G09G 3/3406; G09G 3/36; G09G 2320/0653; G02F 1/134327;
(Continued)

(56) References Cited

U.S. PATENT DOCUMENTS 4,838,661 A    6/1989  McKee et al.
5,384,658 A *  1/1995  Ohtake ..................... C08J 7/02
                                                        359/599
(Continued)

FOREIGN PATENT DOCUMENTS

JP    09265087 A  * 10/1997
JP     9265087 A    10/1997
(Continued)

OTHER PUBLICATIONS

International Search Report and Written Opinion, International Application No. PCT/EP2018/069935, dated Nov. 28, 2018.

Primary Examiner — Jeff Piziali

(57) ABSTRACT

According to an aspect, there is provided a display unit for generating a display output, comprising a first light source; a first back polarizer arranged to polarize light from the first light source in a first polarization direction; a second light source; a second back polarizer arranged to polarize light from the second light source in a second polarization direction that is orthogonal to the first polarization direction; a first substrate; a second substrate; a liquid crystal layer positioned between the first substrate and the second substrate, wherein the first substrate, second substrate and liquid crystal layer are arranged to receive light from the first light source that has been polarized by the first back polarizer and receive light from the second light source that has been polarized by the second back polarizer; and a front polarizer arranged to polarize light, the front polarizer being for polarizing light that has passed through the liquid crystal layer; wherein operating the first light source to generate light generates a positive display output, and operating the second light source to generate light generates a negative display output.

16 Claims, 6 Drawing Sheets

(58) Field of Classification Search
CPC ..... G02F 2001/133567; G02F 2203/64; G02F 1/133528; G02F 1/13362; G02F 2001/133538; G02F 2001/133626; G02F 2203/66; A61N 5/0618

See application file for complete search history.

(56) References Cited

U.S. PATENT DOCUMENTS

| | | | | |
|---|---|---|---|---|
| 2005/0183305 A1* | 8/2005 | Hirata | ............ | G09F 13/04 |
| | | | | 40/615 |
| 2010/0321922 A1* | 12/2010 | Zeinstra | ............ | G09F 13/04 |
| | | | | 362/89 |
| 2011/0227895 A1* | 9/2011 | Takahashi | ............ | G02B 6/0061 |
| | | | | 345/211 |

FOREIGN PATENT DOCUMENTS

| | | |
|---|---|---|
| JP | 2018097233 A | 6/2018 |
| WO | 2009101557 A1 | 8/2009 |

* cited by examiner

DISPLAY UNIT AND A METHOD OF OPERATING THE SAME

CROSS-REFERENCE TO PRIOR APPLICATIONS

This application is the U.S. National Phase application under 35 U.S.C. § 371 of International Application Serial No. PCT/EP2018/069935, filed on 23 Jul. 2018, which claims the benefit of European Application Ser. No. 17182980.7, filed on 25 Jul. 2017. These applications are hereby incorporated by reference herein.

TECHNICAL FIELD OF THE INVENTION

The invention relates to an improved display unit for example for use in an electronic device, such as a light apparatus, and an improved method of operating a display unit.

BACKGROUND TO THE INVENTION

As an alternative to a standard alarm clock, or a phone as an alarm, a so-called wake-up light can be placed on a night stand or bedside table. A wake-up light can be used to gradually increase the intensity of the light produced to help wake a user from sleep more naturally. In some cases, the colour of the light produced by the wake-up light can be adjusted to mimic the colours produced during a sunrise. In addition to providing this lighting or wake-up function, a wake-up light typically also includes a display for displaying information to a user, such as the time, an alarm time, settings for the wake-up light, etc. This information should be visible when the wake-up light is switched off, and when the wake-up light is producing light. The Philips Wake-Up Light HF3520 is an example of this type of wake-up light.

These displays are typically located close to the main illuminating part of the wake-up light (to avoid the wake-up light apparatus being too large), so the display unit has to be designed to enable the information to be visible to a user in all situations that such a light might be used, and particularly when the wake-up light is switched on and generating light. For example, the information should be clearly visible in both the day time and the night time, regardless of whether the wake-up light is switched on and generating light or switched off. These displays typically make use of liquid crystal display (LCD) panels that are backlit to enable the information to be viewed during the night time when the wake-up light source is switched off, and the backlight has to 'compete' with the wake-up light source when the wake-up light source is generating light.

Therefore there is a need for improvements to display units that can be used in wake-up lights and other devices such as light therapy devices and mood-lighting devices in which a display can be integrated to improve the visibility of displayed information to a user in different lighting conditions.

SUMMARY OF THE INVENTION

According to a first aspect, there is provided a display unit for generating a display output, comprising a first light source; a first back polarizer arranged to polarize light from the first light source in a first polarization direction; a second light source; a second back polarizer arranged to polarize light from the second light source in a second polarization direction that is orthogonal to the first polarization direction; a first substrate; a second substrate; a liquid crystal layer positioned between the first substrate and the second substrate, wherein the first substrate, second substrate and liquid crystal layer are arranged to receive light from the first light source that has been polarized by the first back polarizer and receive light from the second light source that has been polarized by the second back polarizer; and a front polarizer arranged to polarize light, the front polarizer being for polarizing light that has passed through the liquid crystal layer, wherein operating the first light source to generate light generates a positive display output, and operating the second light source to generate light generates a negative display output.

In some embodiments, the display unit further comprises a control unit.

In some embodiments, the control unit is configured to switch off or deactivate the second light source while the first light source is generating light to generate the positive display output.

In some embodiments, the control unit is configured to switch off or deactivate the first light source while the second light source is generating light to generate the negative display output.

In some embodiments, the control unit is configured to operate the first light source and the second light source to generate light at the same time to generate a mixed display output.

In some embodiments, the control unit is configured to control the first light source and/or the second light source to adjust the intensity of the light generated thereby, and/or to control the first light source and/or the second light source to adjust the colour of the light generated thereby.

According to a second aspect, there is provided a light apparatus, the light apparatus comprising an outer housing comprising a translucent portion; a display unit as described above, with the display unit arranged to generate the display output on a part of the outer housing, and the first light source of the display unit is arranged such that light generated by the first light source is incident on the translucent portion and on the first substrate, the second substrate and the liquid crystal layer.

In some embodiments, the display unit is arranged to generate the display output on a part of the translucent portion of the outer housing.

In some embodiments, at least the front polarizer of the display unit is comprised in or on the outer housing.

According to a third aspect, there is provided a method of operating a display unit to generate a display output, the display unit comprising a first light source; a first back polarizer arranged to polarize light from the first light source in a first polarization direction; a second light source; a second back polarizer arranged to polarize light from the second light source in a second polarization direction that is orthogonal to the first polarization direction; a first substrate; a second substrate; a liquid crystal layer positioned between the first substrate and the second substrate, wherein the first substrate, second substrate and liquid crystal layer are arranged to receive light from the first light source that has been polarized by the first back polarizer and receive light from the second light source that has been polarized by the second back polarizer; a front polarizer arranged to polarize light in one of the first polarization direction and the second polarization direction, the front polarizer being for polarizing light that has passed through the liquid crystal layer; wherein the method comprises operating the first light source to generate light to generate a positive display output;

and operating the second light source to generate light to generate a negative display output.

In some embodiments, the method further comprises the step of switching off or deactivating the second light source while the first light source is generating light to generate the positive display output.

In some embodiments, the method further comprises the step of switching off or deactivating the first light source while the second light source is generating light to generate the negative display output.

In some embodiments, the method further comprises the step of operating the first light source and the second light source to generate light at the same time to generate a mixed display output.

In some embodiments, the method further comprises the step of controlling the first light source and/or the second light source to adjust the intensity of the light generated thereby, and/or controlling the first light source and/or the second light source to adjust the colour of the light generated thereby.

In some embodiments, the method further comprises the step of providing a gradual transition from the positive display output to the negative display output by gradually reducing the brightness or intensity of the light generated by the first light source and/or gradually increasing the brightness or intensity of the light generated by the second light source.

In some embodiments, the method further comprises the step of providing a gradual transition from the negative display output to the positive display output by gradually reducing the brightness or intensity of the light generated by the second light source and/or gradually increasing the brightness or intensity of the light generated by the first light source.

According to a fourth aspect, there is provided a computer program product comprising a computer readable medium having computer readable code embodied therein, the computer readable code being configured such that, on execution by a suitable computer or processor, the computer or processor is caused to perform any of the methods described above.

In some embodiments, the computer or processor is configured or adapted to operate a display unit as described above.

These and other aspects of the invention will be apparent from and elucidated with reference to the embodiment(s) described hereinafter.

BRIEF DESCRIPTION OF THE DRAWINGS

Exemplary embodiments of the invention will now be described, by way of example only, with reference to the following drawings, in which.

DETAILED DESCRIPTION OF THE EMBODIMENTS

Figure 1:
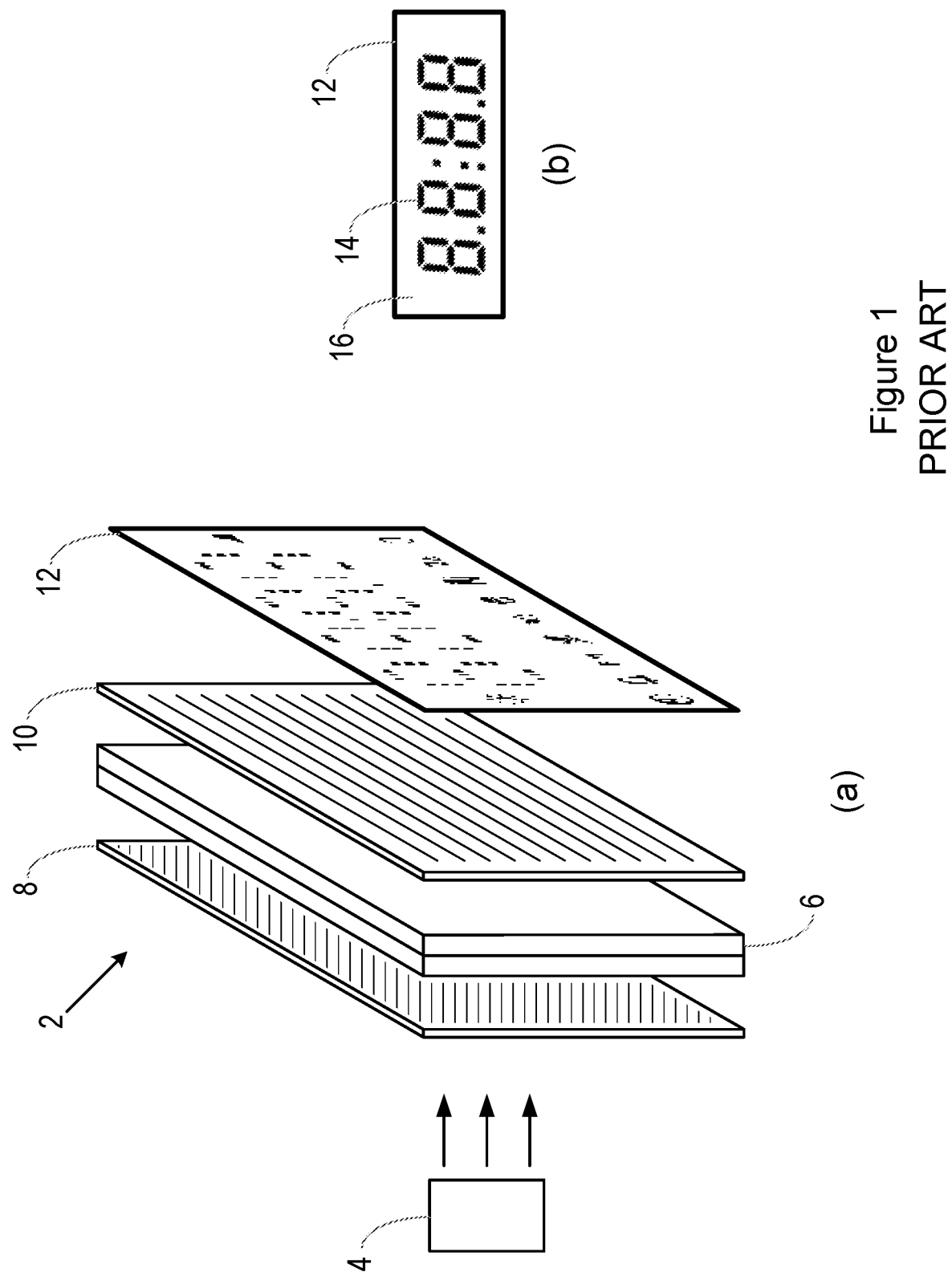
FIG. 1(a) shows a display unit arranged to generate a positive display output and FIG. 1(b) shows a positive display output.
Figure 2:
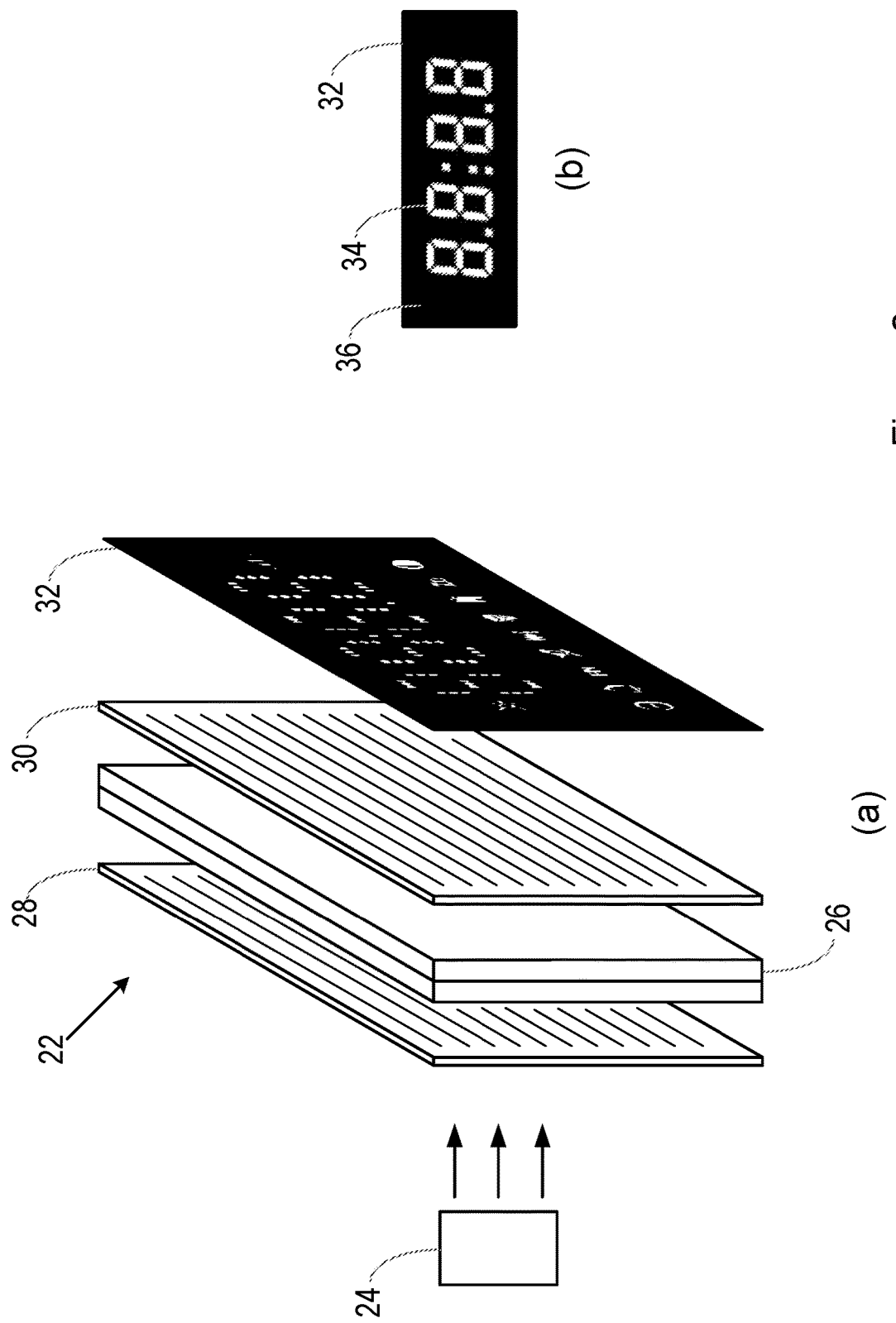
FIG. 2(a) shows a display unit arranged to generate a negative display output and FIG. 2(b) shows a negative display output.

Liquid Crystal Display (LCD) panels are well-known for use in displaying information to a user, and are incorporated into a variety of electronic devices. An LCD panel can be provided with a backlight for providing light to illuminate the LCD panel, with polarizers being used to create the displayed information from light passed by the LCD panel. FIGS. 1 and 2 illustrate two ways in which an LCD panel can be used to display information.

FIG. 1(a) shows one implementation of a conventional LCD-based display unit 2 that creates a so-called 'positive' display output. The display unit 2 comprises a light source 4 (also referred to as a 'backlight' as it is located behind the LCD panel from the user's point of view) and an LCD panel 6 that comprises a layer of liquid crystal sandwiched between two substrates, with the LCD panel 6 being positioned between two polarizers, a back polarizer 8 that is between the backlight 4 and the LCD panel 6 and a front polarizer 10 that is the opposite side of the LCD panel 6 to the backlight 4. The back polarizer 8 and the front polarizer 10 are arranged so that the directions in which they polarize light are orthogonal (i.e. at 90° with respect to each other). For example, as shown in FIG. 1(a), the back polarizer 8 can have a vertical alignment (so light from the backlight 4 is passed to the LCD panel 6 having been polarized in a vertical direction) and the front polarizer 10 can have a horizontal alignment (so only light from the LCD panel 6 that has horizontal components is passed by the front polarizer 10). When there is no electric field applied to the liquid crystal layer in the LCD panel 6, the liquid crystal acts as an optical wave guide and rotates the plane of polarization by a quarter turn (90°) so that the light which reaches the front polarizer 10 can pass through it. An example of a display output 12 produced by this display unit 2 is shown in FIG. 1(a) and FIG. 1(b). Thus, this arrangement produces a positive display output 12 in which the segments 14 that together form the information to be displayed are dark (so the light from the backlight 4 has been blocked by the polarizers 8, 12 and LCD panel 6 for these segments 14) and the background 16 is lit by light from the backlight 4 that has been passed by the polarizers 8, 12 and LCD panel 6. The LCD panel 6 is controlled based on the information to be displayed to determine which of the segments 14 are dark in the positive display output 12.

FIG. 2(a) shows one implementation of a conventional LCD-based display unit 22 that creates a so-called 'negative' display output. A negative display is the opposite to the positive display in that the segments representing the information to be displayed are illuminated and the background is dark. A negative display output can be obtained by arranging the front polarizer and back polarizer so that they polarize light in the same direction. In more detail, the display unit 22 comprises a light source/backlight 24 and an LCD panel 26. The LCD panel 26 is positioned between two polarizers, a back polarizer 28 that is between the backlight 24 and the LCD panel 26 and a front polarizer 30 that is the opposite side of the LCD panel 26 to the backlight 24. The back polarizer 28 and the front polarizer 30 are arranged so that the directions in which they polarize light are the same. For example, as shown in FIG. 2(a), the back polarizer 28 and the front polarizer 30 can both have a horizontal alignment. An example of a display output 32 produced by this display unit 22 is shown in FIG. 2(a) and FIG. 2(b). Thus, this arrangement produces a negative display output 32 in which the segments 34 that together form the information to be displayed are lit by light from the backlight 24 and the remaining segments and the background 36 is dark (so the light from the backlight 24 has been blocked in these parts of the display 32). The LCD panel 26 is controlled based on the information to be displayed to determine which of the segments 34 are lit in the negative display output 32.

Although in the case of graphical LCDs (e.g. dot matrix displays) it is possible to provide a positive display output or a negative display output based on the way in which the pixels are driven (e.g. with a negative display the pixels are inverted with respect to the positive display), typically, the choice of whether to use a positive display output or a negative display output is made during the design of the display unit and cannot be changed (this is particularly the case for segmented displays where the background is not lit). However, in certain applications, such as in a wake-up light or similar apparatus, it can be useful to operate the display unit to provide a positive display output for some of the time and a negative display output for some of the time.

Figure 3:
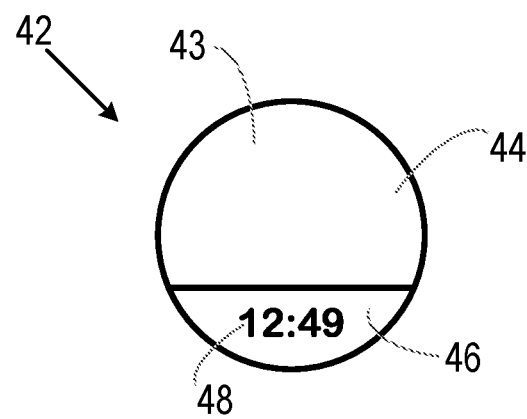
FIG. 3 is a representation of the front of a Philips HF3520 Wake-Up Light.

For example, in the Philips Wake-Up Light HF3520, a front shell (housing) is provided that is illuminated by the main light source of the Wake-Up Light (i.e. the light source that provides the 'wake-up' light) and an LCD-based display unit having its own backlight is provided is a lower part of the front of the device that is not illuminated by the main light source. This is illustrated in FIG. 3. FIG. 3 is a representation of the front of the Philips HF3520 Wake-Up Light, with the wake-up light 42 comprising a housing 43 having an illuminating portion 44 that is for illumination by a main light source of the light 42 and a display portion 46 on which information 48, such as the time, is displayed. The illuminating portion 44 and display portion 46 are both translucent portions of the housing 43 (and indeed in the Philips HF3520 the entire front face is a single translucent shell), although the display portion 46 is not illuminated by the main light source of the wake-up light 42. In the Philips HF3520 Wake-Up Light the display unit behind the display portion 46 is configured to generate a negative display output so that the background of the display does not stand out against the (unilluminated) display portion 46 when the wake-up light is generating the 'wake-up' light, and so that the display portion 46 does not emit light more light than necessary when the wake-up light is not generating light (e.g. in the night time when the environment is dark).

Since the display portion 46 of the housing 43 is not illuminated by the light source that illuminates the illuminating portion 44, the presence of the display portion 46 either increases the overall size of the wake-up light 42 (to maintain the illuminating portion 44 at the same brightness) or requires a brighter light to produce the same level of light output as a larger illuminating portion 44 (in which case the brightness of the display portion 46 may also need to be increased to ensure that it is still visible when the wake-up light is on).

Figure 4:
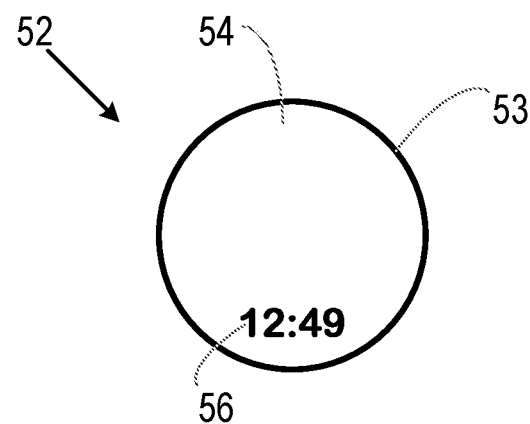
FIG. 4 is a representation of the front of an exemplary light apparatus.

Therefore it is desirable to be able to provide a light apparatus in which the display information/display output can be shown on the illuminating portion 44, rather than in a separate display portion 46. A representation of the front view of such an apparatus is shown in FIG. 4. This light apparatus 52 comprises a housing 53 or shell having a translucent portion 54 (the entire front surface in this example), and information 56 is displayed in or on the translucent portion 54 by a display unit inside the housing 53 so that it is visible to a user looking at the light apparatus 52. It will be appreciated that the circular shape of the front surface of the light apparatus 52 is merely exemplary, and other shapes or configurations can be used. Likewise, although this example shows the translucent portion 54 as the whole of the front surface, it will be appreciated that other designs are possible, for example the translucent portion 54 could have a border.

Thus, in this exemplary apparatus 52, to provide the 'clean' display of the information 56 when the main light source of the light apparatus 52 is illuminating the translucent portion 54 (i.e. without showing the background part of the LCD panel), the display unit inside the apparatus 52 should operate to provide a positive display, with the display unit backlight providing light for the background of the positive display output having the same colour and brightness as the surrounding parts of the translucent portion 54 that are illuminated by the main light source of the light apparatus 52. However, matching the light output by the main light source and the light output by a display unit can be difficult to achieve in practice, and, as noted above, the positive display output is not optimal for when the main light source is switched off (and particularly when the environment around the apparatus 52 is dark), and a negative display output would be preferred.

Those skilled in the art will appreciate that the way in which the pixels or segments in an LCD display are driven can determine whether a positive or negative display output is provided. In the case of a full pixel/segment display (i.e. where all elements of a LCD panel are driven/controllable), inverting the way in which pixels or segments are driven (so an active pixel or segment becomes an inactive pixel or segment and vice versa) can still provide a useful display of the information (e.g. as seen from FIGS. 1(b) and 2(b)). However, this is not the case for a display where the background 16, 36 is not driven/controllable, since then only the active/inactive pixels/segments would be inverted, and this can lead to the information becoming incorrect or unreadable. In addition, inverting the control of the active/inactive pixels/segments to provide a positive display output and a negative display output is not suitable when the display unit is used in a light apparatus such as a wake-up light when the light source is not generating light all of the time, and thus an alternative mechanism for switching between a positive display output and a negative display output is needed. Furthermore, by controlling the pixels to make them either positive or negative, the possibility of providing a gradual change will depend on the level of grey scale or number of colours. When the display is monochrome, it is only possible to switch in one step from positive to negative, and vice versa.

Therefore, the invention addresses these problems by providing a display unit that can be controlled to selectively provide a positive display output and a negative display output, and that is suitable for use in a light apparatus in which information is to be displayed while the main light source of the light apparatus is generating light, and when the main light source of the light apparatus is not generating light. Thus, a light apparatus, such as a wake-up light, light therapy device or mood lighting device, that includes the display unit according to the invention can provide for the display of information in the form of a positive display output on a part of the housing of the apparatus that is illuminated by a main light source when the main light source is active, and providing a display of information in the form of a negative display output when the main light source is not active (or vice versa depending on the design requirements for the light apparatus).

Figure 5:
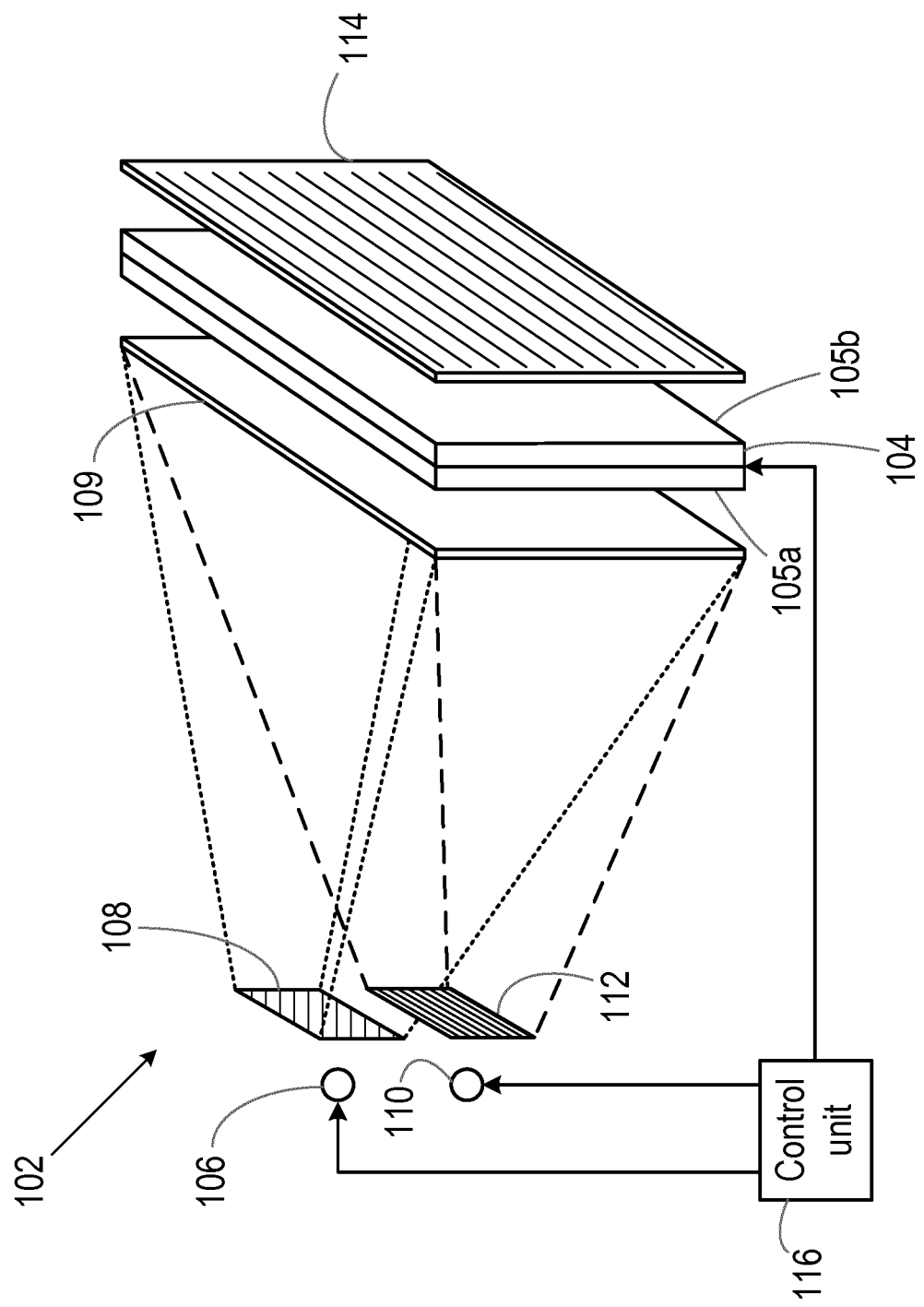
FIG. 5 is a diagram illustrating a display unit according to an embodiment of the invention.

According to the invention, an LCD panel is provided with two light sources that are selectively used to cause the display unit to provide a positive display output and a negative display output. An exemplary embodiment of a display unit according to the invention is shown in FIG. 5.

Thus, the display unit 102 comprises an LCD panel 104 that comprises a layer of liquid crystal sandwiched or positioned between two substrates 105a, 105b. The substrates 107a, 107b can be formed from glass or any other suitable material and one or both of the substrates 105a, 105b can comprise a plurality of electrodes, with each electrode being associated with a particular pixel or display segment of the LCD panel 104. As is conventional, the electrode or electrodes on the substrates 105a, 105b corresponding to a particular pixel or segment can be used to change or set the polarization direction of the liquid crystal for that pixel or segment in the liquid crystal layer, thereby affecting the output of the display unit 102. In some embodiments, the liquid crystal layer can be such that when there is no electric field applied to the (or part of the) liquid crystal layer (e.g. by the electrodes), the liquid crystal acts as an optical wave guide and rotates the plane of polarization of incident light by a quarter turn (90°). In these embodiments, when an electric field is applied to the (or part of the) liquid crystal layer, the liquid crystal aligns with the electric field and the liquid crystal no longer rotates the plane of polarization of incident light. In alternative embodiments, the liquid crystal layer can be such that when there is no electric field applied to the (or part of the) liquid crystal layer, the liquid crystal acts as an optical wave guide and rotates the plane of polarization of incident light by an amount other than a quarter turn (e.g. 45°), and when an electric field is applied the liquid crystal acts to rotate the plane of polarization of incident light by a corresponding amount (e.g. −45°) in order to effect a rotation of the light by 90° compared to when no electric field is applied.

The display unit 102 also comprises a first light source 106 (also referred to as a first 'backlight') and a first back polarizer 108 that is between the first light source 106 and the LCD panel 104. The first back polarizer 108 is arranged to polarize light from the first light source 106 in a first polarization direction. In the exemplary arrangement shown in FIG. 5, the first back polarizer 108 has a vertical alignment (so polarizes light in a vertical direction), although it will be appreciated that any other polarization direction can be used. The first light source 106 can be a light emitting diode (LED) based light source that includes one or more LEDs. The one or more LEDs can comprise LEDs having one or more colours that are controllable individually and/or in combination to produce light of a desired colour and/or light of a desired brightness or luminance. As an alternative to LEDs, the first light source 106 could be one or more organic LEDs (OLEDs), halogen bulbs, incandescent bulbs or low-pressure mercury bulbs.

The display unit 102 also comprises a diffuser or diffusing panel 109 that is positioned or located between the LCD panel 104 and the first back polarizer 108. The diffuser 109 acts to diffuse or 'spread' light incident thereon so that the LCD panel 104 is more evenly lit by the incident light. It will be appreciated that in some embodiments the diffuser 109 may be in a different location in the display unit 102, e.g. so that the light exiting the LCD panel 104 passes through the diffuser 109.

The first light source 106 and first back polarizer 108 are arranged so that light emitted or generated by the first light source 106 is polarized by the first back polarizer 108 and this polarized light is incident on the LCD panel 104 via the diffuser 109.

In addition to the first light source 106 and first back polarizer 108, the display unit 102 comprises a second light source 110 and a second back polarizer 112. The second light source 110 is also referred to as a second 'backlight'. The second back polarizer 112 is provided between the second light source 110 and the diffuser 109 and LCD panel 104. The second back polarizer 112 is provided to polarize light from the second light source 110 in a second polarization direction. The second light source 110 and second back polarizer 112 are arranged so that light emitted or generated by the second light source 110 is polarized by the second back polarizer 112 and this polarized light is incident on the LCD panel 104 via the diffuser 109. The second light source 110 can be a light emitting diode (LED) based light source that includes one or more LEDs. The one or more LEDs can comprise LEDs having one or more colours that are controllable individually and/or in combination to produce light of a desired colour and/or light of a desired brightness or luminance. As an alternative to LEDs, the second light source 110 could be one or more organic LEDs (OLEDs), halogen bulbs, incandescent bulbs or low-pressure mercury bulbs.

So that light from the second light source 110 can be used to form a display in the opposite display mode to the first light source 106, the second polarization direction is orthogonal to the first polarization direction of the first back polarizer 108 (i.e. the second polarization direction is rotated by 90° with respect to the first polarization direction). In the exemplary arrangement shown in FIG. 5, the first back polarizer 108 has a vertical alignment/vertical polarization direction and therefore the second back polarizer 112 has a horizontal alignment/horizontal polarization direction. Of course, it will be appreciated that other polarization directions can be used, provided that the polarization direction of the first back polarizer 108 is opposite (i.e. orthogonal) to the polarization direction of the second back polarizer 112.

It should be noted that the first light source 106 and first back polarizer 108 form a separate optical path to the second light source 110 and the second back polarizer 112 in the sense that light from the first light source 106 does not pass through the second back polarizer 112 towards the diffuser 109 and LCD panel 104, and light from the second light source 110 does not pass through the first back polarizer 108 towards the diffuser 109 and LCD panel 104. In some implementations, the first light source 106 can be substantially or completely optically isolated from the second back polarizer 112 so that light from the first light source 106 cannot be incident on the second back polarizer 112, and likewise the second light source 110 can be substantially or completely optically isolated from the first back polarizer 108 so that light from the second light source 110 cannot be incident on the first back polarizer 108.

The display unit 102 also comprises a front polarizer 114 that is arranged on the opposite side of the LCD panel 104 to the light sources 106, 110. The front polarizer 114 is arranged to polarize the light that has transmitted or passed through the LCD panel 104 to generate the display output. The polarization direction of the front polarizer 114, and the way in which the pixels/segments of the LCD panel 104 are driven will determine which of the first light source 106 and second light source 110 are used to provide the positive display output and the negative display output.

In the exemplary arrangement shown in FIG. 5, the front polarizer 114 has the same polarization direction as the second back polarizer 112, i.e. the opposite polarization direction to the polarization direction of the first back polarizer 108 (although it will be appreciated that the polarization direction of the front polarizer 114 can be different depending on the effect that the liquid crystal in the LCD panel 104 has on the incident light). Therefore, with the pixels/segments in the LCD panel 104 being driven appropriately, light from the first light source 106 can form a positive display output (e.g. as shown in FIG. 1(*b*)) after it has passed through the first back polarizer 108, the LCD panel 104 and the front polarizer 114, and light from the second light source 110 can form a negative display output (e.g. as shown in FIG. 2(*b*)) after it has passed through the second back polarizer 112, the LCD panel 104 and the front polarizer 114. With the driving of the pixels/segments in the LCD panel 104 being inverted with respect to the above, light from the first light source 106 can form a negative display output (e.g. as shown in FIG. 2(*b*)) after it has passed through the first back polarizer 108, the LCD panel 104 and the front polarizer 114, and light from the second light source 110 can form a positive display output (e.g. as shown in FIG. 1(*b*)) after it has passed through the second back polarizer 112, the LCD panel 104 and the front polarizer 114. It should be noted that, in either case above, the LCD panel 104 is driven the same way regardless of which of the first light source 106 and the second light source 110 is generating light (i.e. the way in which the LCD panel 104 is driven is not inverted when the active light source 106, 110 is changed). In other words, the control signals used to display certain information (e.g. a particular time) will be the same regardless of whether the display output is positive or negative. According to the invention, the switch between the positive display output and the negative display output is caused simply by switching the light source 106, 110 that is generating the light for the LCD panel 104.

It will be appreciated by those skilled in the art that if the polarization direction of the front polarizer 114 was the same polarization direction as the first back polarizer 108 and thus opposite to the polarization direction of the second back polarizer 112 (with the LCD panel 104 being driven in the same way), the light from the first light source 106 will form the negative display output (e.g. as shown in FIG. 2(*b*)), and light from the second light source 110 will form the positive display output (e.g. as shown in FIG. 1(*b*)).

Finally, the display unit 102 in FIG. 5 comprises a control unit 116. The control unit 116 can be for controlling the LCD panel 104 to cause the display of the required information (e.g. by providing suitable control signals to electrodes on the first substrate 105*a* and/or second substrate 105*b*. In some embodiments, the control unit 116 can control the first light source 106 and/or second light source 110. In particular, the control unit 116 can control the activation and deactivation of the first light source 106 and second light source 110. In addition, or alternatively, the activation and deactivation of at least one of the first light source 106 and second light source 110 can be controlled by a user of the display unit 102.

In further embodiments, the control unit 116 can be configured to control or adjust the brightness or intensity of the light generated by the first light source 106 and/or the light generated by the second light source 110. The control unit 116 may also or alternatively be configured to control or adjust the colour of the light generated by the first light source 106 and/or the light generated by the second light source 110.

The control unit 116 can be implemented in numerous ways, with software and/or hardware, to perform the various functions described herein. The control unit 116 may comprise one or more microprocessors or digital signal processor (DSPs) that may be programmed using software or computer program code to perform the required functions and/or to control components of the control unit 116 to effect the required functions. The control unit 116 may be implemented as a combination of dedicated hardware to perform some functions (e.g. amplifiers, pre-amplifiers, analog-to-digital convertors (ADCs) and/or digital-to-analog convertors (DACs)) and a processor (e.g., one or more programmed microprocessors, controllers, DSPs and associated circuitry) to perform other functions. Examples of components that may be employed in various embodiments of the present disclosure include, but are not limited to, conventional microprocessors, DSPs, application specific integrated circuits (ASICs), and field-programmable gate arrays (FPGAs).

In various implementations, the control unit 116 may be associated with or comprise one or more memory units (not shown) such as volatile and non-volatile computer memory such as RAM, PROM, EPROM, and EEPROM. The control unit 116 or associated memory unit can also be used for storing program code that can be executed by a processor in the control unit 116 to perform the method described herein.

Figure 6:
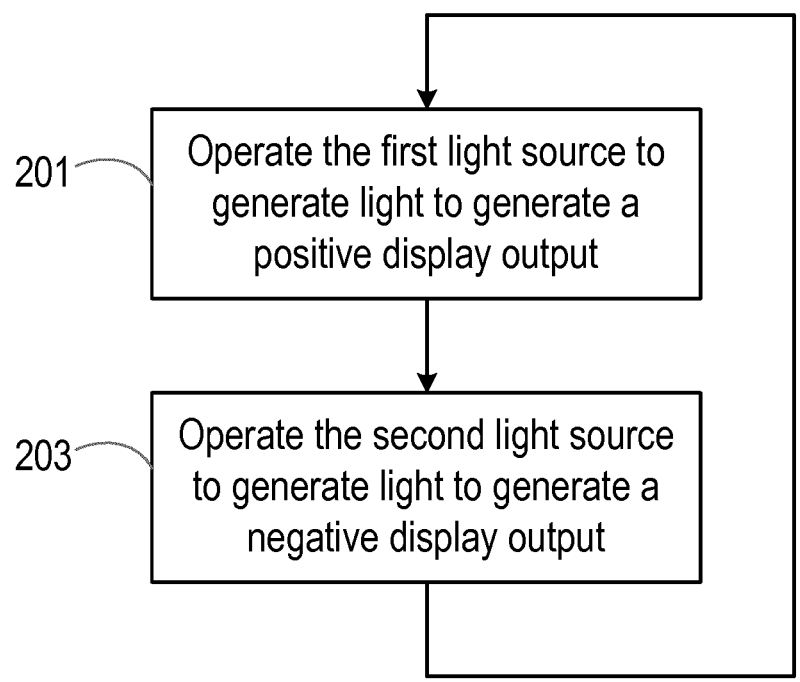
FIG. 6 is a flow chart illustrating a method of operating the display unit of FIG. 5.

The flow chart in FIG. 6 illustrates a method of operating the display unit 102 according to an embodiment of the invention.

In a first step of the method, step 201, the first light source 106 is operated to generate light, and this generates a positive display output from the display unit 102. In another step, step 203, the second light source 110 is operated to generate light, and this generates a negative display output from the display unit 102. Thus, selection of the light source determines whether the display unit 102 generates a positive display output or a negative display output.

It will be appreciated that steps 201 and 203 do not have to be performed in the order shown, and the display unit 102 can be operated to generate a negative display output followed by a positive display output.

In some embodiments of the method, the control of the display 'mode' of the display unit 102 (i.e. whether the display output is positive or negative), is simply a result of which of the first light source 106 and second light source 110 is generating light. This control can therefore be provided by a user manually activating a light source 106, 110 or by a user selecting a preference for the type of display output (i.e. positive or negative). In other embodiments, the method can be performed by the control unit 116. In these embodiments, the control unit 116 may determine which of the light sources to activate, for example based on ambient lighting conditions, an alarm timer, etc.

In some implementations, the display unit 102 can be configured such that when the first light source 106 is deactivated/switched off, the second light source 110 is automatically activated/switched on, and vice versa. In this way at least one of the light sources will be active all of the time, thereby providing a display output for a user.

In some embodiments, when the first light source 106 is operated to generate light, the control unit 116 can switch off or deactivate the second light source 110, so that the light from the first light source 106 can generate the positive display output. In some embodiments, when the second light source 110 is operated to generate light, the control unit 116 can switch off or deactivate the first light source 106, so that the light from the second light source 110 can generate the negative display output.

In some embodiments, the first light source and the second light source can be operated at the same time. This will result in a 'mixed' display output. The display output is mixed in the sense that it is not a pure positive display output (as shown in FIG. 1(*b*)) or a pure negative display output (as shown in FIG. 2(*b*)). For example, the background of the display can have the colour of the first light source 106 and the active segments/pixels can have the colour of the second light source 110 (or vice versa). In some embodiments, which can be particularly useful when the display unit 102 is used in a wake-up light or other light apparatus where the brightness of a main light source is gradually increased or decreased, the control unit 116 can adjust the brightness or intensity of each of the light sources 106, 110 in order to provide a gradual transition from a positive display output to a negative display output (or vice versa).

For example, to provide a gradual transition from a positive display output to a negative display output, the control unit 116 can gradually reduce the brightness or intensity of the light generated by the first light source 106 while gradually increasing the brightness or intensity of the light generated by the second light source 110. To provide a gradual transition from a negative display output to a positive display output, the control unit 116 can gradually reduce the brightness or intensity of the light generated by the second light source 110 while gradually increasing the brightness or intensity of the light generated by the first light source 106. It will be appreciated that in either of these examples, the brightness or intensity of one of the light sources can be adjusted while the brightness or intensity of the other one of the light sources is kept constant. This may be useful where one of the light sources has a much higher default brightness or intensity level than the other light source.

Figure 7:
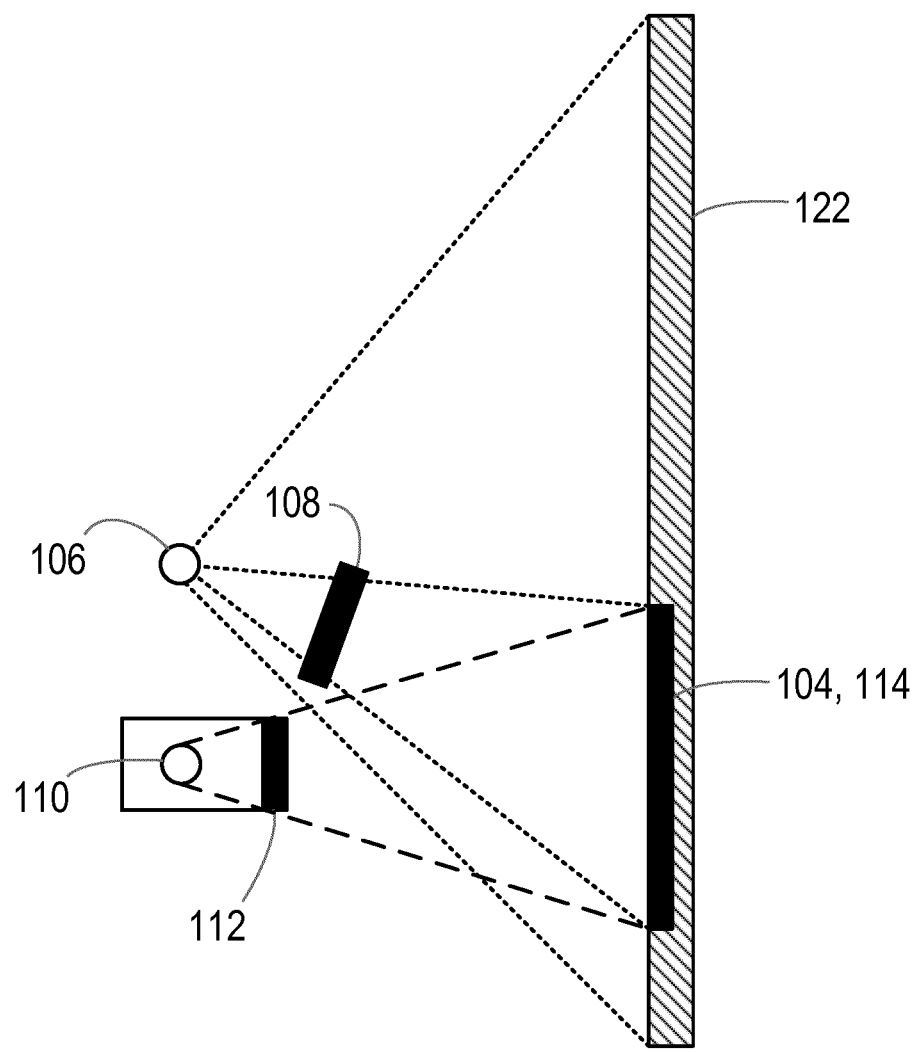
FIG. 7 is a diagram illustrating a light apparatus that includes a display unit according to an embodiment of the invention.

FIG. 7 shows an exemplary use of a display unit 102 in a light apparatus, such as a wake-up light. The light apparatus 120 comprises an outer housing or shell that has a translucent portion. Information (such as the time, an alarm time or apparatus settings, etc.) is to be displayed in or on a part of the translucent portion 122 by a display unit 102 inside the housing so that it is visible to a user looking at the light apparatus 120. The front polarizer 114 of the display unit 102, and optionally also the LCD panel 104 of the display unit 102, can be integrated into the translucent portion 122 of the housing or placed adjacent to the translucent portion 122 (either on the inside or outside of the housing). The translucent portion 122 preferably has diffusing properties (unless the display unit 102 comprises a diffusing panel 109). The translucent portion 122 of the housing can be formed from a plastic, such as polycarbonate, which can include a filler or colouring compound, or a more transparent material, such as Polymethyl methacrylate (PMMA) or glass. The filler preferably has high reflective properties to minimise losses due to light being absorbed in the translucent portion 122. One example of a filler is titanium dioxide, although those skilled in the art will be aware of other types of filler that can be used.

As noted above, the first light source 106 of the display unit 102 can provide a positive display output (so a lit background and dark pixels/segments). When the display unit 102 is used in a light apparatus 120, in addition to this function, the first light source 106 can also be the main light source for the light apparatus 120. Thus, the first light source 106 provides the main illumination of the translucent portion 122. In this way, when the first light source 106 is activated and generating light, the first light source 106 will illuminate the translucent portion 122 and also provide the backlight for the LCD panel 104 in the display unit 102. Therefore, the positive display output will be backlit by the same light source (i.e. with the same colour and approximately the same brightness) that illuminates the rest of the translucent portion 122 thereby providing an apparent 'seamless' positive display output on the translucent portion 122. The second light source 110 is provided in the display unit 102 to provide the backlight for the LCD panel 104 when the main light source of the light apparatus 120 is switched off. Thus, when the main light source is switched off (e.g. in the night time for a wake-up light), the second light source 110 is switched on and provides the information as a negative display output.

In embodiments where the display unit 102 is used in a light apparatus 120 where the negative display output is to be used in a dark environment, the colour of the second light source 110 can be selected to optimise readability without resulting in a high level of illumination. For example the colour of the second light source 110 can be amber or red, although those skilled in the art will appreciate that other colours could be used, including white.

In some embodiments (particularly in the case of a wake-up light), the control unit 116 (which is not shown in FIG. 6) can control the colour of the light generated by the first light source 106, for example to mimic the colours of a sunrise. The control unit 116 may also or alternative control the colour of the light generated by the second light source 110.

As noted above, in some embodiments the control unit 116 can be configured to adjust the intensity or brightness of the light generated by the first light source 106 and/or the second light source 110. This enables the control unit 116 to effect a gradual transition from the positive display output to a negative display output, or vice versa, for example when a wake-up light is gradually increasing the brightness of the light generated.

It will be appreciated that the colour of the light generated by the first light source 106 will determine the colour of the background and inactive pixels/segments in the positive display output, and the colour of the light generated by the second light source 110 will determine the colour of the active segments/pixels in the negative display output. Therefore, the use of two backlight sources for the LCD panel 104 means that different colour configurations of the display output can be provided. These colour configurations can be preset during manufacture, or set according to a user setting or user preference. In one example, in the negative mode the background of the display output can be black with the segments or pixels conveying the information being a selected colour (e.g. white, yellow, red, blue, etc.). In another example, in the positive display mode the segments or pixels conveying the information (i.e. the activated pixels/segments) can be black with the background having a selected colour. In yet another example, the background can have a selected colour and the segments or pixels conveying the information (i.e. the activated pixels/segments) can have a different selected colour (which is the case with a mixed output).

There is therefore provided an improved display unit that can be used to provide a positive display output or a negative display output based on which one of two backlight sources of the display unit is activated.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A display unit for generating a display output, comprising:
   a first light source;
   a first back polarizer arranged to polarize light from the first light source in a first polarization direction;
   a second light source;
   a second back polarizer arranged to polarize light from the second light source in a second polarization direction that is orthogonal to the first polarization direction;
   wherein the first light source and the second light source are arranged such that light from the first light source does not pass through the second back polarizer and light from the second light source does not pass through the first back polarizer;
   a first substrate;
   a second substrate;
   a liquid crystal layer positioned between the first substrate and the second substrate, wherein the liquid crystal layer is arranged to receive, at a first point on the liquid crystal layer, light from the first light source that has been polarized by the first back polarizer and receive, at the first point on the liquid crystal layer, light from the second light source that has been polarized by the second back polarizer; and
   a front polarizer arranged to polarize light, the front polarizer being for polarizing light that has passed through the liquid crystal layer to generate the display output;
   wherein light from the first light source causes the display unit to generate a positive display output, and light from the second light source causes the display unit to generate a negative display output.

2. A display unit as claimed in claim 1, wherein the display unit further comprises a control unit.

3. A display unit as claimed in claim 1, wherein the control unit is configured to switch off or deactivate the second light source while the first light source is generating light to generate the positive display output.

4. A display unit as claimed in claim 2, wherein the control unit is configured to switch off or deactivate the first light source while the second light source is generating light to generate the negative display output.

5. A display unit as claimed in claim 2, wherein light from both the first light source and the second light source generates the display output as a mixed display output.

6. A display unit as claimed in claim 2, wherein the control unit is configured to control the first light source and/or the second light source to adjust an intensity of light generated thereby, and/or to control the first light source and/or the second light source to adjust a colour of light generated thereby.

7. A light apparatus, the light apparatus comprising:
   an outer housing comprising a translucent portion;
   a display unit as claimed in claim 1, wherein the display unit is arranged to generate the display output on a part of the outer housing;
   wherein the first light source of the display unit is arranged such that light generated by the first light source is incident on the translucent portion and on the first substrate, the second substrate and the liquid crystal layer.

8. A light apparatus as claimed in claim 7, wherein the display unit is arranged to generate the display output on a part of the translucent portion of the outer housing.

9. A light apparatus as claimed in claim 7, wherein at least the front polarizer of the display unit is comprised in or on the outer housing.

10. A method of operating a display unit to generate a display output, the display unit comprising a first light source; a first back polarizer arranged to polarize light from the first light source in a first polarization direction; a second light source; a second back polarizer arranged to polarize light from the second light source in a second polarization direction that is orthogonal to the first polarization direction; wherein the first light source and the second light source are arranged such that light from the first light source does not pass through the second back polarizer and light from the second light source does not pass through the first back polarizer; a first substrate; a second substrate; a liquid crystal layer positioned between the first substrate and the second substrate, wherein the liquid crystal layer is arranged to receive, at a first point on the liquid crystal layer, light from the first light source that has been polarized by the first back polarizer and receive, at the first point on the liquid crystal layer, light from the second light source that has been polarized by the second back polarizer; a front polarizer arranged to polarize light in one of the first polarization direction and the second polarization direction, the front polarizer being for polarizing light that has passed through the liquid crystal layer to generate the display output; wherein the method comprises:
   operating the first light source to generate light to cause the display unit to generate a positive display output; and
   operating the second light source to cause the display unit to generate a negative display output.

11. A method as claimed in claim 10, wherein the method further comprises the step of:
   switching off or deactivating the second light source while the first light source is generating light to generate the positive display output.

12. A method as claimed in claim 10, wherein the method further comprises the step of:
   switching off or deactivating the first light source while the second light source is generating light to generate the negative display output.

13. A method as claimed in claim 10, wherein the method further comprises the step of:
   controlling the first light source and/or the second light source to adjust an intensity of light generated thereby, and/or controlling the first light source and/or the second light source to adjust a colour of light generated thereby.

14. A method as claimed in claim 10, wherein the method further comprises the step of:
   providing a transition from the positive display output to the negative display output by reducing the brightness or intensity of the light generated by the first light source and/or increasing the brightness or intensity of the light generated by the second light source.

15. A method as claimed in claim 10, wherein the method further comprises the step of:
   providing a transition from the negative display output to the positive display output by reducing the brightness or intensity of the light generated by the second light source and/or increasing the brightness or intensity of the light generated by the first light source.

16. A computer program product comprising a computer readable medium having computer readable code embodied therein, the computer readable code being configured such that, on execution by a computer or processor, the computer or processor is caused to perform the method of claim 10.

* * * * *